(12) United States Patent
Davies et al.

(10) Patent No.: US 8,092,450 B2
(45) Date of Patent: Jan. 10, 2012

(54) MAGNETICALLY GUIDABLE ENERGY DELIVERY APPARATUS AND METHOD OF USING SAME

(75) Inventors: Gareth Davies, Toronto (CA); Kelly Albert, Mississauga (CA); Gareth Torrey Munger, Kirkwood, MO (US); Ashwini Pandey, Collinsville, IL (US); Raju Viswanathan, Clayton, MO (US)

(73) Assignees: Baylis Medical Company Inc., Montreal (CA); Stereotaxis, Inc., St. Louis, MO (US)

( * ) Notice: Subject to any disclaimer, the term of this patent is extended or adjusted under 35 U.S.C. 154(b) by 1352 days.

(21) Appl. No.: 11/627,406

(22) Filed: Jan. 26, 2007

(65) Prior Publication Data

US 2007/0123964 A1    May 31, 2007

Related U.S. Application Data

(60) Provisional application No. 60/743,181, filed on Jan. 27, 2006, provisional application No. 60/827,458, filed on Sep. 29, 2006.

(51) Int. Cl.
*A61B 18/18* (2006.01)

(52) U.S. Cl. ............... 606/41; 607/116; 606/38

(58) Field of Classification Search ............... 606/20–52; 128/898; 600/373; 607/116
See application file for complete search history.

(56) References Cited

U.S. PATENT DOCUMENTS

| | | | |
|---|---|---|---|
| 4,244,362 A | 1/1981 | Anderson | |
| 4,790,311 A | 12/1988 | Ruiz | |
| 4,790,809 A | 12/1988 | Kuntz | |
| 4,807,620 A | 2/1989 | Strul et al. | |
| 5,019,076 A | 5/1991 | Yamanashi et al. | |
| 5,318,525 A | 6/1994 | West et al. | |
| 5,364,393 A | 11/1994 | Auth et al. | |
| 5,397,304 A | 3/1995 | Truckai | |
| 5,425,382 A | 6/1995 | Golden et al. | |
| 5,622,169 A | 4/1997 | Golden et al. | |

(Continued)

FOREIGN PATENT DOCUMENTS

WO    WO 00/19917 A1    4/2000

(Continued)

OTHER PUBLICATIONS

Lepage, Lewis, Ruiz, Yamanishi, Padron, Hood. Angiopyroplasty using Electromagnetically Induced Focused Heat. Angiology. Jul. 1987;38(7):520-3.

(Continued)

*Primary Examiner* — Linda Dvorak
*Assistant Examiner* — Amanda Scott
(74) *Attorney, Agent, or Firm* — Dowell & Dowell, P.C.

(57) ABSTRACT

An energy delivery apparatus for delivering electrical energy at a target location, the energy delivery apparatus being usable in combination with a magnetic field. The energy delivery apparatus includes an electrical conductor, the electrical conductor having a substantially elongated configuration; an electrode for delivering the electrical energy at the target location, the electrode being electrically coupled to the electrical conductor and located at a predetermined location therealong; and a guiding element mounted to the electrical conductor in a substantially spaced apart relationship relative to the electrode, the guiding element including a magnetically responsive material. The energy delivery apparatus is constructed such that a movement of the guiding element causes a corresponding movement of the electrode. The magnetic field is used to move the guiding element in order to position the electrode substantially adjacent to the target location.

15 Claims, 12 Drawing Sheets

U.S. PATENT DOCUMENTS

| | | | |
|---|---|---|---|
| 5,624,430 | A | 4/1997 | Eton et al. |
| 5,779,688 | A * | 7/1998 | Imran et al. ............... 604/533 |
| 5,885,227 | A | 3/1999 | Finlayson |
| 5,916,210 | A | 6/1999 | Winston et al. |
| 5,931,818 | A | 8/1999 | Werp et al. |
| 5,944,023 | A | 8/1999 | Johnson et al. |
| 5,951,482 | A | 9/1999 | Winston et al. |
| 5,964,757 | A * | 10/1999 | Ponzi ........................... 606/45 |
| 5,989,276 | A * | 11/1999 | Houser et al. ............... 606/170 |
| 6,013,072 | A | 1/2000 | Winston et al. |
| 6,048,349 | A | 4/2000 | Winston et al. |
| 6,063,093 | A | 5/2000 | Winston et al. |
| 6,106,515 | A | 8/2000 | Winston et al. |
| 6,155,264 | A | 12/2000 | Ressemann et al. |
| 6,193,676 | B1 | 2/2001 | Winston et al. |
| 6,210,408 | B1 | 4/2001 | Chandrasekaran et al. |
| 6,221,061 | B1 | 4/2001 | Engelson et al. |
| 6,228,076 | B1 | 5/2001 | Winston et al. |
| 6,292,678 | B1 | 9/2001 | Hall et al. |
| 6,304,769 | B1 | 10/2001 | Arenson et al. |
| 6,385,472 | B1 | 5/2002 | Hall et al. |
| 6,394,976 | B1 | 5/2002 | Winston et al. |
| 6,428,551 | B1 | 8/2002 | Hall et al. |
| 6,485,485 | B1 | 11/2002 | Winston et al. |
| 6,508,754 | B1 | 1/2003 | Liprie et al. |
| 6,524,303 | B1 | 2/2003 | Garibaldi |
| 6,554,827 | B2 | 4/2003 | Chandrasekaran et al. |
| 6,662,034 | B2 | 12/2003 | Segner et al. |
| 6,663,621 | B1 | 12/2003 | Winston et al. |
| 6,709,444 | B1 | 3/2004 | Makower |
| 6,733,511 | B2 | 5/2004 | Hall et al. |
| 6,740,103 | B2 | 5/2004 | Hall et al. |
| 6,752,800 | B1 | 6/2004 | Winston et al. |
| 6,755,816 | B2 | 6/2004 | Ritter et al. |
| 6,820,614 | B2 | 11/2004 | Bonutti |
| 6,834,201 | B2 * | 12/2004 | Gillies et al. ............... 600/411 |
| 6,842,639 | B1 | 1/2005 | Winston et al. |
| 6,852,109 | B2 | 2/2005 | Winston et al. |
| 6,855,143 | B2 | 2/2005 | Davison et al. |
| 6,911,026 | B1 * | 6/2005 | Hall et al. .................... 606/28 |
| 6,951,554 | B2 | 10/2005 | Johansen et al. |
| 6,970,732 | B2 | 11/2005 | Winston et al. |
| 6,980,843 | B2 | 12/2005 | Eng et al. |
| 2001/0012934 | A1 | 8/2001 | Chandrasekaran et al. |
| 2002/0019644 | A1 * | 2/2002 | Hastings et al. ............. 606/159 |
| 2004/0116851 | A1 | 6/2004 | Johansen et al. |
| 2004/0133130 | A1 | 7/2004 | Ferry et al. |
| 2005/0004585 | A1 | 1/2005 | Hall et al. |
| 2005/0010208 | A1 | 1/2005 | Winston et al. |
| 2005/0096529 | A1 * | 5/2005 | Cooper et al. ............... 600/407 |
| 2005/0119556 | A1 * | 6/2005 | Gillies et al. ............... 600/410 |
| 2005/0261607 | A1 | 11/2005 | Johansen et al. |
| 2005/0288631 | A1 * | 12/2005 | Lewis et al. ............... 604/98.01 |
| 2006/0089638 | A1 | 4/2006 | Carmel et al. |

FOREIGN PATENT DOCUMENTS

| | | |
|---|---|---|
| WO | WO 01/17600 A1 | 3/2001 |
| WO | WO 01/93939 A1 | 12/2001 |

OTHER PUBLICATIONS

Hausdorf, Schulze-Neick, Lange. Radiofrequency-Assisted "reconstruction" of the Right Ventricular Outflow Tract in Muscular Pulmonary Atresia with Ventricular Septal Defect. British Heart Journal. Apr. 1993;69(4):343-6.

Hausdorf, Schneider, Lange. Catheter Creation of an Open Outflow Tract in Previously Atretic Right Ventricular Outflow Tract Associated with Ventricular Septal Defect. The Americal Journal of Cardiology. Aug. 1, 1993;72(3):354-6.

Fink, Peuster, Bertram, Hausdorf. Transcatheter Recanalization of the Left Main Pulmonary Artery after Four Years of Complete Occlusion. Catheterization and Cardiovascular Interventions. May 2001;53(1):81-4.

Kort, Balzer. Radiofrequency Perforation in the Treatment of Acquired Left Pulmonary Artery Atresia Following Repair of Tetralogy of Fallot. Catheterization and Cardiovascular Interventions. Sep. 2003;60(1):79-81.

Pedra, Mont'Alverne Filho, Arrieta, Tellez, Fontes. Recanalization of a Discrete Atretic Right Pulmonary Artery Segment with a New Radiofrequency System. Catheterization and Cardiovascular Interventions. Sep. 2003;60(1):82-7.

Levi, Alejos, Moore. Future of Interventional Cardiology in Pediatrics. Current Opinion in Cardiology. Mar. 2003;18(2):79-90.

Veldtman, Hartley, Visram, Benson. Radiofrequency Applications in Congenital Heart Disease. Expert Rev Cardiovasc Ther. Jan. 2004;2(1):117-26.

Holzer, Hardin, Hill, Chisolm, Cheatham. Radiofrequency Energy—A Multi-Facetted Tool for the Congenital Interventionist. Congenital Cardiology Today. Jun. 2006; 4(6): 1-.

* cited by examiner

MAGNETICALLY GUIDABLE ENERGY DELIVERY APPARATUS AND METHOD OF USING SAME

REFERENCES TO PARENT AND CO-PENDING APPLICATIONS

This application claims the benefit of U.S. provisional patent application Ser. No. 60/743,181, filed Jan. 27, 2006 and U.S. provisional patent application Ser. No. 60/827,458, filed Sep. 29, 2006. All of these US patent applications are hereby incorporated by reference in their entirety.

FIELD OF THE INVENTION

The present invention relates generally to methods and devices usable to deliver energy. More specifically, the present invention is concerned with a magnetically guidable energy delivery apparatus and methods of using same.

BACKGROUND OF THE ART

Many medical interventions rely on the delivery to a target location of energy, such as electrical energy, inside the body of a patient. For example, an occlusion in a blood vessel may be vaporized, at least partially, by delivering a suitable electrical current to the occlusion.

There currently exist magnetically guided guide wires, which are typically relatively long and relatively thin wires at the end of which a magnet is located. The guide wire is typically used in conjunction with a catheter that is slid over the guide wire after the wire has been advanced through a desired path. In use, the guide wire is protruding over a relatively small distance in front of the catheter when there is a need to either steer the catheter at a junction, or guide the catheter through a relatively tortuous path. Then, a magnetic field may be applied to guide the guide wire through a predetermined path and thereafter slide the catheter over the guide wire. However, such guide wires are typically not well suited to the targeted application of electrical energy as, for example, they are not electrically insulated.

Against this background, there exists a need in the industry to provide novel methods and apparatuses for delivering energy using a magnetically guidable device. An object of the present invention is therefore to provide such a method and an apparatus.

SUMMARY OF THE INVENTION

In a broad aspect, the invention provides an energy delivery apparatus for delivering electrical energy at a target location, the energy delivery apparatus being usable in combination with a magnetic field. The energy delivery apparatus includes an electrical conductor, the electrical conductor having a substantially elongated configuration; an electrode for delivering the electrical energy at the target location, the electrode being electrically coupled to the electrical conductor and located at a predetermined location therealong; and a guiding element mounted to the electrical conductor in a substantially spaced apart relationship relative to the electrode, the guiding element including a magnetically responsive material. The energy delivery apparatus is constructed such that a movement of the guiding element causes a corresponding movement of the electrode. The magnetic field is used to move the guiding element in order to position the electrode substantially adjacent to the target location.

Advantageously, the energy delivery apparatus is relatively flexible and relatively small, and may therefore be inserted through relatively tortuous paths inside the body of the patient and also may be inserted through relatively small body vessels.

Spacing apart the guiding element from the electrode substantially prevents de-magnetization of the magnetically responsive material present in the guiding element caused by heating of materials substantially adjacent the electrode when electrical current is delivered by the electrode.

In some embodiments of the invention, a heat shield is located between the electrode and the guiding element. This improves the thermal insulation between these two components and therefore further prevents de-magnetization of the magnetically responsive material present in the guiding element.

In another broad aspect, the invention provides a method for delivering electrical energy at a target location using an energy delivery apparatus, the method using a magnetic field, the target location being located in a body of a patient, the body including a body vessel, the energy delivery apparatus being substantially elongated, the energy delivery apparatus defining an apparatus proximal end and a substantially longitudinally opposed apparatus distal end, the energy deliver apparatus including a substantially elongated electrical conductor, an electrode electrically coupled to the electrical conductor and a magnetically responsive material mounted to the electrical conductor. The method includes: inserting the apparatus distal end into the body vessel; applying the magnetic field to exert a magnetic force onto the magnetically responsive material so as to move the electrode; guiding the electrode to an electrode location, the electrode location being substantially adjacent to the target location; and delivering the electrical energy at the target location through the electrode.

In yet another broad aspect, the invention provides an energy delivery apparatus for delivering electrical energy at a target location, the energy delivery apparatus being usable in combination with a magnetic field. The energy delivery apparatus includes an electrical conductor, the electrical conductor having a substantially elongated configuration; an electrode for delivering the electrical energy at the target location, the electrode being electrically coupled to the electrical conductor; and a guiding element mounted to the electrical conductor, the guiding element including a magnetically responsive material. The energy delivery apparatus is constructed such that a movement of the guiding element causes a corresponding movement of the electrode. The magnetic field is used to move the guiding element in order to position the electrode substantially adjacent to the target location.

Other objects, advantages and features of the present invention will become more apparent upon reading of the following non-restrictive description of certain embodiments thereof, given by way of example only with reference to the accompanying drawings.

BRIEF DESCRIPTION OF THE DRAWINGS

In order that the invention may be readily understood, embodiments of the invention are illustrated by way of examples in the accompanying drawings, in which.

DETAILED DESCRIPTION

With specific reference now to the drawings in detail, it is stressed that the particulars shown are by way of example and for purposes of illustrative discussion of certain embodiments of the present invention only, and are presented in the cause of providing what is believed to a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Also, for the purposes of this description, proximal indicates next to or nearer to an intended user of the apparatus described herein, and distal indicates further away from the intended user.

Figure 1:
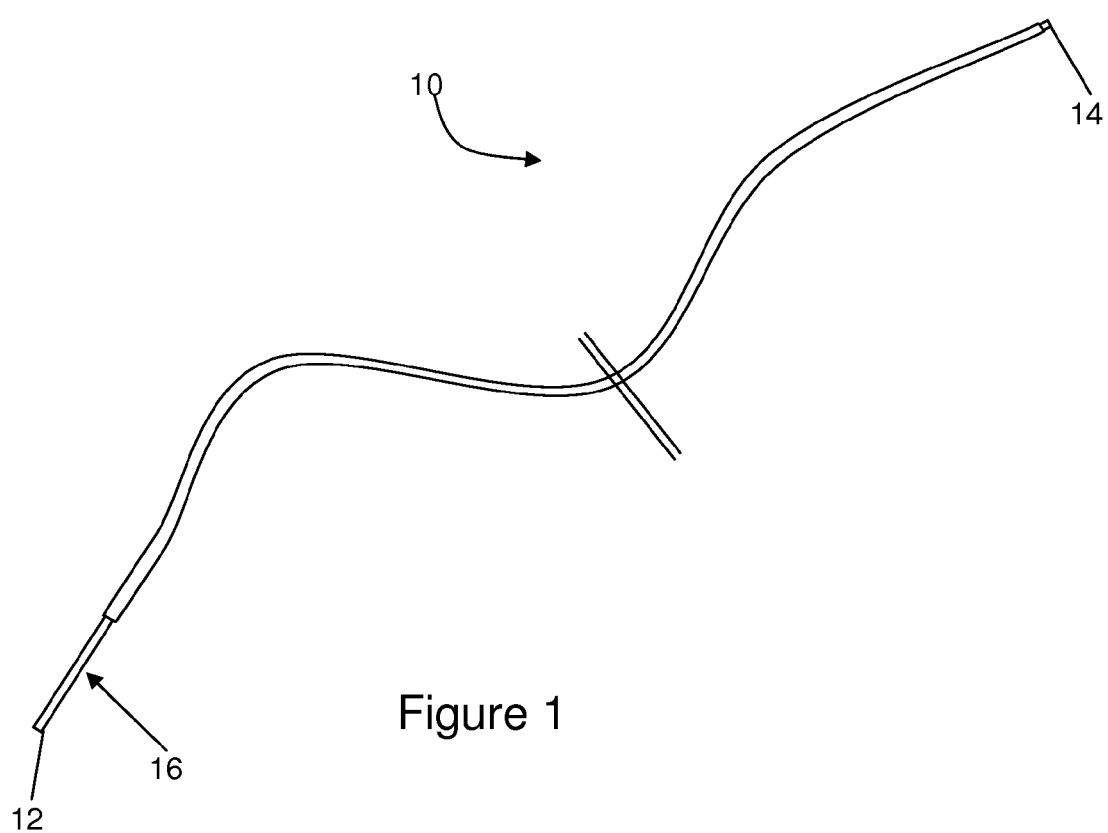
FIG. 1, in a side elevation view, illustrates an energy delivery apparatus in accordance with an embodiment of the present invention.

With reference to FIG. 1, there is shown an embodiment of an energy delivery apparatus 10 for delivering electrical energy at a target location. For example, and non-limitingly, the target location is located inside the body of a patient. The energy delivery apparatus 10 is usable in combination with a magnetic field (not shown in the drawings). The magnetic field allows to guide the energy delivery apparatus 10 so that a predetermined component or portion of the energy delivery apparatus, such as for example an electrode, is located substantially adjacent the target location. The energy delivery apparatus 10 is substantially elongated and defines an apparatus proximal end 12 and a substantially longitudinally opposed apparatus distal end 14. The apparatus proximal end 12 is typically configured and sized so as to be couplable to a conventional source of electrical energy.

Figure 2:
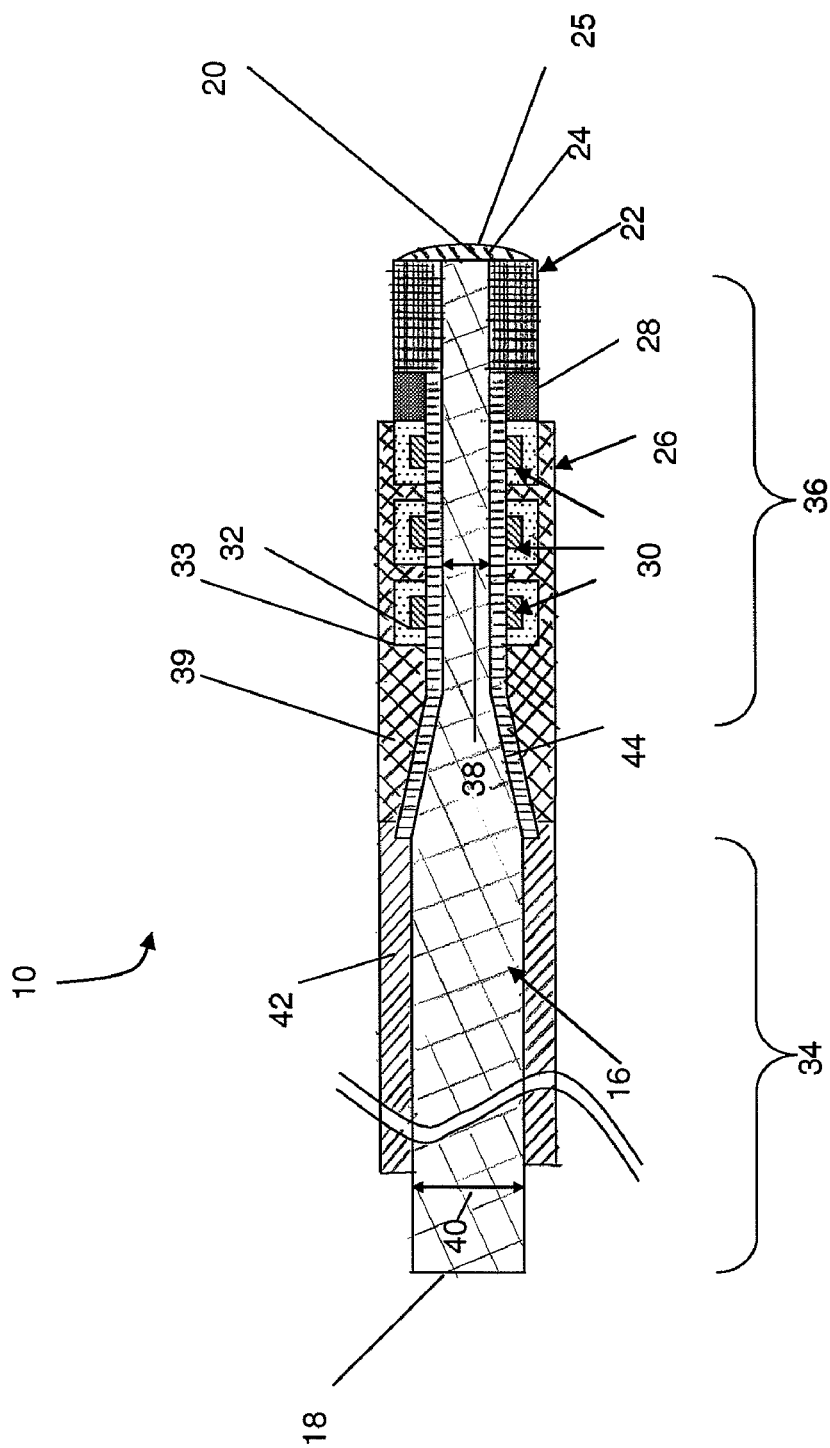
FIG. 2, in a partial side cross-sectional view, illustrates the energy delivery apparatus shown in FIG. 1.

Referring to FIG. 2, the energy delivery apparatus 10 includes a substantially elongated electrical conductor 16, which may be any suitable conductor, such as a wire or a cable made out of a suitable electrically conducting material, such as for example, Nitinol, stainless steel, gold, platinum, titanium, silver or alloys thereof. The electrical conductor 16 is substantially elongated and defines a conductor proximal end 18 and a substantially longitudinally opposed conductor distal end 20. An electrode 22 is electrically coupled to the electrical conductor 16 and located at a predetermined location therealong, for example adjacent to conductor distal end 20. The electrode 22 is provided for delivering electrical energy at a target location.

A guiding element 26 is mechanically coupled or otherwise directly or indirectly mounted to the electrical conductor 16 in a substantially spaced apart relationship relative to the electrode 22. The guiding element 26 includes a magnetically responsive material. The energy delivery apparatus 10 is constructed such that movements of the guiding element 26 cause corresponding movements of the electrode 22. The magnetic field is therefore usable to move the guiding element 26 in order to position the 22 substantially adjacent to the target location. A more detailed description of a method of magnetic navigation is disclosed in U.S. Pat. No. 6,755,816 B2 (issued on 29 Jun. 2004), which is hereby incorporated by reference in its entirety.

Spacing apart the guiding element 26 from the 22 ensures that any temperature increase caused by the delivery of electrical energy to the target location only minimally influences the magnetic properties of the guiding element 26. Indeed, some materials, such as for example permanently magnetized materials, have a temperature over which they lose their magnetic properties. For many of the magnetically responsive materials that are suitable for use with the energy delivery apparatus 10, this temperature is sufficiently low that thermal effects caused by the delivery of the electrical energy could contribute significantly to this loss of magnetic properties.

In the embodiment of the invention shown in FIG. 2, the guiding element 26 is substantially longitudinally spaced apart from the electrode 22. More specifically, the electrode 22 is located distally relatively to the guiding element 26. For example, the electrode 22 is located substantially adjacent to the conductor distal end 20. It should be noted that while the electrode 22 shown in FIG. 2 is substantially cylindrical and extends substantially radially outwardly from the electrical conductor 16, it is also within the scope of the invention to have an electrode that is formed integrally by a section of the outermost surface of the electrical conductor 16.

The electrode 22 defines an electrode tip 24. In this embodiment, the electrode tip 24 defines tip distal surface 25 that is shaped substantially similarly to a portion of a sphere, i.e. rounded. This helps to ensure that injuries that may be caused to the body vessels, through movements of the electrode tip 24 through these vessels, are minimized.

In some embodiments of the invention, the energy delivery apparatus 10 includes an electrically insulating material substantially covering the electrical conductor 16, such as for example and non-limitingly, Teflons®, such as polytetrafluoroethylene (PTFE), fluorinated ethylene propylene copolymer (FEP), perfluoroalkoxy (PFA), or ethylene and tetrafluoroethylene copolymer (ETFE, for example Tefzel®), or coatings other than Teflons®, such as polyetheretherketone plastics (PEEK™), parylene, certain ceramics, or polyethylene terpthalate (PET). In some embodiments, the electrically insulating material forms a layer that extends substantially radially outwardly from the electrical conductor 16. The electrically insulating material is described in further details hereinbelow. In some embodiments, at least a portion of the electrode 22 is substantially deprived of the electrically insulating material so as to allow delivery of an electrical energy therethrough.

In some embodiments of the invention, the energy delivery apparatus 10 further includes a heat shield 28 made out of a substantially thermally insulating material, for example, and non-limitingly, polytetrafluoroethylene (PTFE), which has a thermal conductivity of about 0.3 W/m-K. In this embodiment, the heat shield 28 may have a thickness of at least about 0.025 mm. In other embodiments, the thickness of the heat shield 28 may vary, depending on the thermal conductivity of the material being used. The heat shield 28 is located, at least in part, between the electrode 22 and the guiding element 26. The heat shield 28 is provided for further thermally insulating the guiding element 26 from the electrode 22 and from heat produced by the delivery of electrical energy through the electrode 22.

In some embodiments of the invention, the heat shield includes polytetrafluoroethylene (PTFE). The use of PTFE is advantageous as, in addition to having suitable thermal insulation properties, PTFE is also an electrically insulating material (having a dielectric strength of about 24 kV/mm) and, therefore, contributes to the prevention of arcing between the electrode 22 and any metallic material that may be present in the guiding element 26. In alternate embodiments, other materials, such as for example, Zirconium Oxide, may be used for heat shield 28.

In the embodiment of the invention shown in FIG. 2, the heat shield 26 extends substantially longitudinally from both the guiding element 26 and the electrode 22. In other words, the heat shield 28 substantially fills a gap between the electrode 22 and the guiding element 26. However, in alternative embodiments of the invention, the heat shield 28 extends substantially longitudinally only from one of the guiding element 26 and the electrode 22 or, alternatively, the heat shield 26 does not contact either one of the guiding element 26 and the electrode 22. An advantage of having a heat shield 28 that extends from and contacts both the electrode 22 and the guiding element 26 is that the electrodes 22 are then located as close as possible to the guiding element 26 which therefore helps in improving the precision with which the electrode 22 is guided through the magnetic field interacting with the guiding element 26.

As shown in the drawings, typically, the guiding element 26 and the heat shield 28 are both substantially annular and extend substantially radially outwardly away from the electrically insulating material covering the electrical conductor 16. In a very specific embodiment of the invention, the electrode 22, the heat shield 28 and the guiding element 26 are all substantially annular and have substantially similar outer diameters. This configuration results in an energy delivery apparatus 10 for which a distal region thereof has a substantially uniform outer diameter, which therefore facilitates navigation of the energy delivery apparatus 10 through body vessels and the creation of channels through occlusions and other biological tissues inside the patient. However, in alternative embodiments of the invention, the heat shield 28, the electrode 22 and the guiding element 26 may all have any other suitable diameters.

In some embodiments of the invention, the guiding element 26 includes one or more guiding components 30. For example, as shown in FIG. 2, the guiding element 26 includes three substantially longitudinally spaced apart guiding components 30. Each of the guiding components 30 includes a respective magnetically responsive material. In the illustrated embodiment, having the guiding components 30 spaced apart provides additional flexibility around guiding element 26. In some embodiments of the invention, the guiding components 30 are substantially adjacent to each other. In such a configuration, having more than one guiding component allows to have a guiding element that is more responsive to a given magnetic field while ensuring that the radial extension of the guiding element 26 is relatively small. In alternative embodiments of the invention, the guiding components 30 are spaced apart further from each other in a manner allowing to control the shape of the electrical conductor 16. In other words, in these embodiments, it is possible to apply magnetic fields having different orientations substantially adjacent each of the guiding components 30 to control the shape of the electrical conductor 16. While the use of three guiding components 30 in the energy delivery apparatus 10 has been found to be optimal using commonly available magnetic materials, it is within the scope of the invention to have guiding elements 22 having less than three or more than three guiding components 30.

In some embodiments of the invention, the guiding components 30 include permanently magnetized components such as, for example a neodymium magnet, a platinum-cobalt magnet, or any other suitable heat-resistant magnets. A heat resistant magnet, for the purpose of this description, is defined as a magnet that has relatively low probabilities of being adversely affected in its magnetization by a delivery of electrical energy through the electrode 22. However, in alternative embodiments of the invention, each of the guiding components 30 includes any other suitable magnetically responsive material such as, for example, a ferromagnetic, a paramagnetic, or a diamagnetic material.

Also, in some embodiments of the invention, each of the guiding components 30 includes a substantially annular magnet 32 coated by a protective coating 33, such as a parylene coating. The protective coating 33 ensures biocompatibility between the guiding components 30 and the body in which the energy delivery apparatus 10 is inserted. In alternative embodiments of the invention, the protective coating 33 is any other suitable biocompatible coating. Also, in some embodiments of the invention, an additional coating 39 is provided over one or more of the electrode 22, the heat shield 28 and the guiding components 30. This additional coating 39 may help to secure components 30 in place, may provide additional lubricity (e.g. it may be hydrophilic) and may be filled with a radiopaque filler for improved visualization. In one particular embodiment, the additional coating 39 is made of a polyurethane, for example Tecoflex®, Carbothane® or carboflex and it extends between the individual components 30 such that the guiding element 26 has a substantially longitudinally constant outer diameter.

In some embodiments of the invention, the electrical conductor 16 defines a conductor wider section 34 and a conductor narrower section 36. The conductor narrower section 36 is positioned distally relatively to the conductor wider section 34. The conductor wider section 34 has a cross-sectional area that is substantially larger than the cross-sectional area of the conductor narrower section 36. The conductor narrower section 36 increases the flexibility of the distal end section of the energy delivery apparatus 10 while the conductor wider section 34 allows for maintaining a relatively large rigidity at the proximal end of the energy delivery apparatus 10. This allows to relatively easily steer the conductor distal end 20 while allowing to relatively easily manipulate the energy delivery apparatus into the body vasculature of the patient. In addition, having a conductor wider section 34 of a relatively large cross-sectional area reduces ohmic losses when the electrical current is delivered to the electrode 22.

In some embodiments of the invention, the conductor wider and narrower sections 34 and 36 are substantially cylindrical and define respective conductor wider and narrower section outer diameters 38 and 40. Therefore, in these embodiments, the conductor wider section outer diameter is substantially larger than the conductor narrower section outer diameter. A conductor narrower section having a conductor narrower section outer diameter of about 0.0025 inches or less has been found to be particularly well suited for use in relatively small body vessels.

In alternative embodiments of the invention, the electrical conductor 16 is made more flexible substantially adjacent the conductor distal end 20 than substantially adjacent the conductor proximal end 18 in any other suitable manner such as, for example, by using different materials for manufacturing the conductor proximal and distal regions. It has been found that a suitable material for manufacturing the actual conductor 16 is Nitinol. Indeed, Nitinol shows super-elastic properties and is therefore particularly suitable for applying relatively large deformations thereto in order to guide the energy delivery apparatus 10 through relatively tortuous paths. Also, since the energy delivery apparatus 10 typically creates channels inside biological tissues through radio frequency perforations, in some embodiments of the invention, the energy delivery apparatus 10 typically does not need to be very rigid.

In some embodiments of the invention, the electrically insulating material is divided into a first electrically insulating material and a second electrically insulating material. A first electrically insulating layer 42 made out of the first electrically insulating material substantially covers a first section of the electrical conductor 16. A second electrically insulating layer 44 made out of the second electrically insulating material substantially covers a second section of the electrical conductor 16. The second section is located distally relatively to the first section. Furthermore, the first and second electrically insulating materials may comprise different materials with differing physical properties. For example, in some embodiments, the second electrically insulating material comprises polyimide, while the first electrically insulating material comprises PTFE. This allows for the second electrically insulating layer 44 to be substantially thinner than the first electrically insulating layer 42, while being sufficiently insulative so as to prevent undesired leakage of current. This substantially increases the flexibility of the energy delivery apparatus 10 substantially adjacent the apparatus distal end 14. In addition, this provides a material that is substantially more lubricious over the wider section of the energy delivery apparatus 10 so as to facilitate movement of the energy delivery apparatus 10 through body vessels and through channels created within the body.

Typically, the first electrically insulating layer 42 substantially covers the conductor wider section 34 and the second electrically insulating layer 44 substantially covers the conductor narrower section 36. However, in alternative embodiments of the invention, the first and second electrically insulating layers 42 and 44 are configured in any other suitable manner. Also, to ensure maximal electrically insulating properties while minimizing stress concentrations that may cause cracks in the electrically insulating layer provided by the first and second electrically insulating layers 42 and 44, in some embodiments of the invention, the first electrically insulating layer 42 substantially overlaps the second electrically insulating layer 44 at their junction. Also, in alternative embodiments of the invention, the electrical conductor 16 is electrically insulated in any other suitable manner.

In some embodiments of the invention, a radiopaque marker is mounted to the electrical conductor 16. In some embodiments of the invention, the radiopaque marker is also the magnetically responsive material present in the guiding elements 26. However, in alternative embodiments of the invention, the radiopaque marker includes a radiopaque material that is distinct from the guiding element 26 and that is secured to conductor 16 or secured or embedded into the electrically insulating layer, among other possibilities. For example, FIGS. 6A to 6F respectively illustrate embodiments of the invention wherein a radiopaque band 47 is mounted around the electrode 22, at the proximal-most portion of the electrode 22, a radiopaque band 47' is mounted under the heat shield 28 and a radiopaque coil 47" is wrapped around the distalmost portion of the energy delivery apparatus 10.

Figure 3:
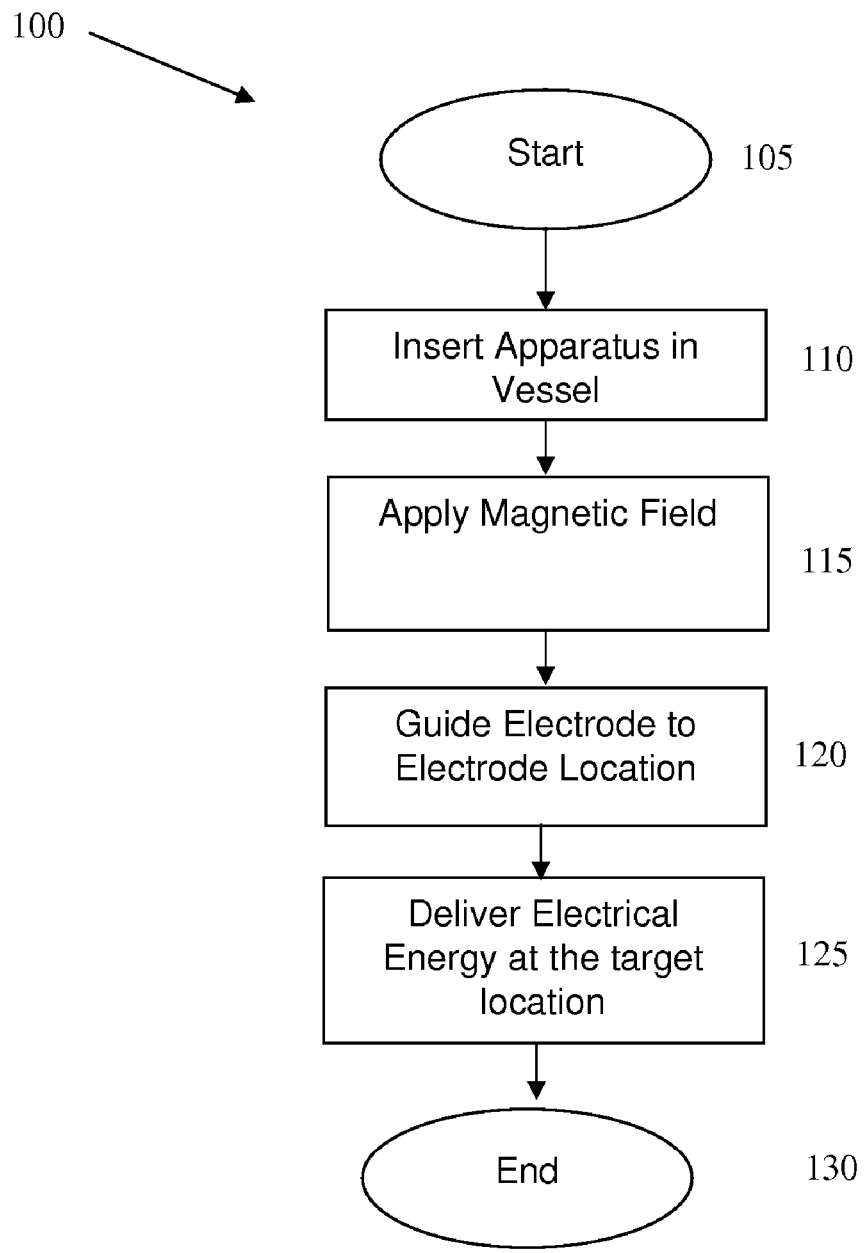
FIG. 3, in a flowchart, illustrates an embodiment of a method of the present invention.
Figure 4A:
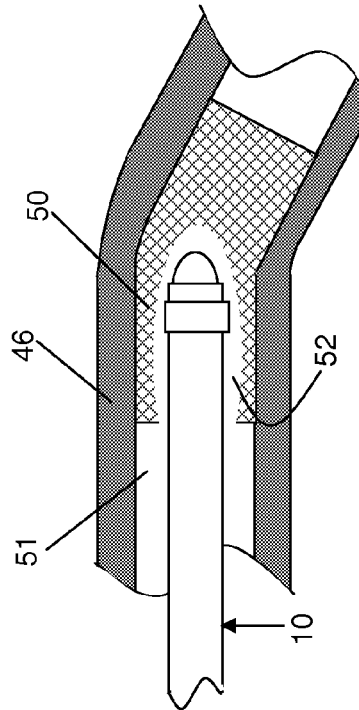
FIGS. 4A through 4D illustrate successive steps in an embodiment of a method of the present invention in which the distal end of the apparatus is steered while creating a channel through an occlusion.
Figure 4B:
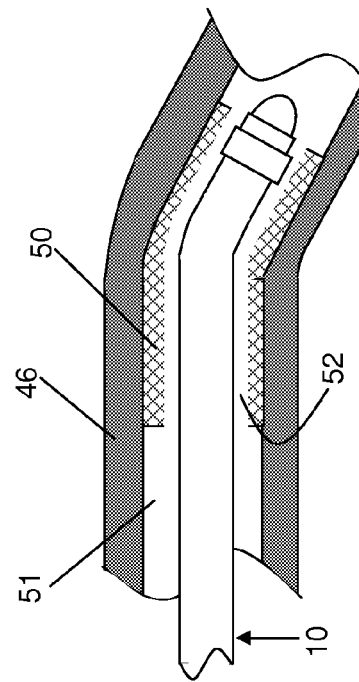
Figure 4C:
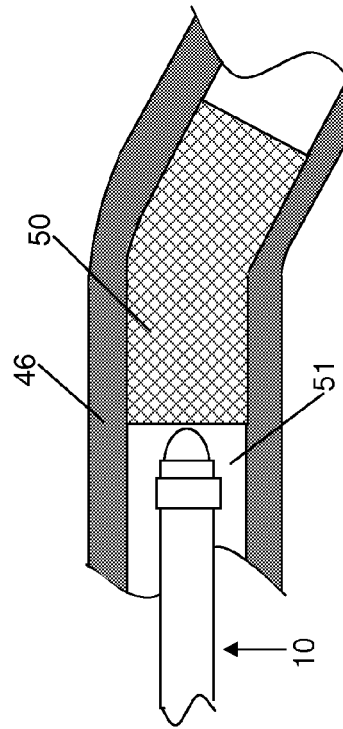
Figure 4D:
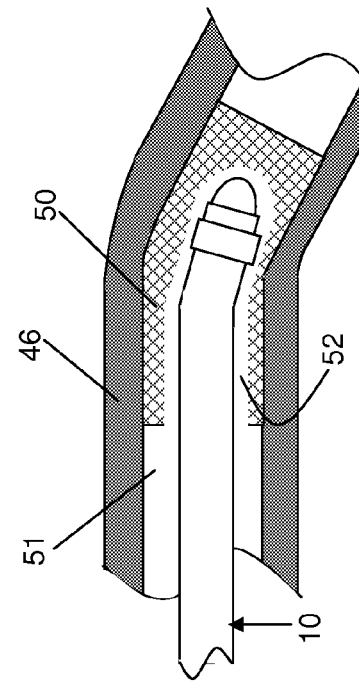

FIG. 3, in a flowchart, illustrates a method 100 for delivering electrical energy at the target location using the energy delivery apparatus 10 and a magnetic field. FIGS. 4A to 4D and 5A to 5E illustrate specific examples of implementation of the method 100. In these examples, the target location is located in the body of a patient. The body includes a body vessel 46, 46' defining a lumen 51, 51' and the energy delivery apparatus may be the energy delivery apparatus 10 or any other suitable energy delivery apparatus. The method starts at step 105. Then, at step 110, the apparatus distal end 14 is inserted into the body vessel 46, 46'. Afterwards, when required, the magnetic field is applied to exert a magnetic force onto the magnetically responsive material so as to move the electrode 22 at step 115. Then, at step 120, the electrode 22 is guided to an electrode location, the electrode location being substantially adjacent to the target location. Afterwards, at step 125, the electrical energy is delivered at the target location through the electrode 22 and the method ends at step 130.

In some embodiments of the invention, delivering the electrical energy and applying the magnetic field are performed substantially simultaneously. Such embodiments allow for guiding the electrode while a channel or perforation is created, for example. In other words, as shown for example in FIG. 5, applying the magnetic field while delivering energy allows for greater control over the creation of the channel or perforation at the target location. However, in alternate embodiments of the invention, the delivery of energy and the application of the magnet field occur partially concurrently while, in further embodiments, the delivery of energy and the application of the magnetic field occur at substantially different points in time, for example substantially sequentially.

In some embodiments, advancing the apparatus through the body and applying the magnetic field are performed substantially simultaneously. However, in alternate embodiments of the invention, advancing the apparatus and the application of the magnet field occur partially concurrently while, in further embodiments, advancing the apparatus and the application of the magnetic field occur at substantially different points in time, for example substantially sequentially. For example, in some embodiments, the magnetic field is applied when the apparatus distal end is advanced through the body vessel 46, 46' and arrives at a bifurcation in the body vessel 46, 46'. Then, the magnetic field may be applied to select which branch of the body vessel 46, 46' will be entered by the apparatus distal end 14, and the apparatus distal end 14 is then further advanced through the body vessel 46, 46' to enter the selected branch. In these embodiments, the apparatus distal end 14 is advanced into the body vessel 46, 46' while substantially simultaneously applying the magnetic field.

In some embodiments of the invention, the target location is included in an occlusion 50, the occlusion 50 at least partially occluding the body vessel 46, 46'. It has been found that many types of body vessels 46, 46' that are typically not accessible using conventional energy delivery apparatuses, such as coronary blood vessels, peripheral blood vessels and cranial blood vessels, among other possibilities, are relatively easily accessible using the energy delivery apparatus 10. Therefore, the presence of the electrode 22 and of the guiding element 26 in the energy delivery apparatus 10 produce a synergistic effect allowing to perform surgical procedures that were typically not able to be performed using prior art energy delivery apparatuses.

In some embodiments of the invention, the energy delivery apparatus 10 is used such that a channel 52 is created at least partially through the occlusion. This channel may be created by delivering energy through the electrode 22 and advancing the apparatus distal end into the occlusion 50 simultaneously or after delivering energy. In some embodiments of the invention, as shown in FIGS. 4A to 4D, and more specifically in FIG. 4C, advancing the apparatus distal end and applying the magnetic field are performed substantially simultaneously. In these embodiments, the shape of a channel 52 created inside the body vessel 46 may therefore be controlled through the application of a magnetic field.

Figure 5A:
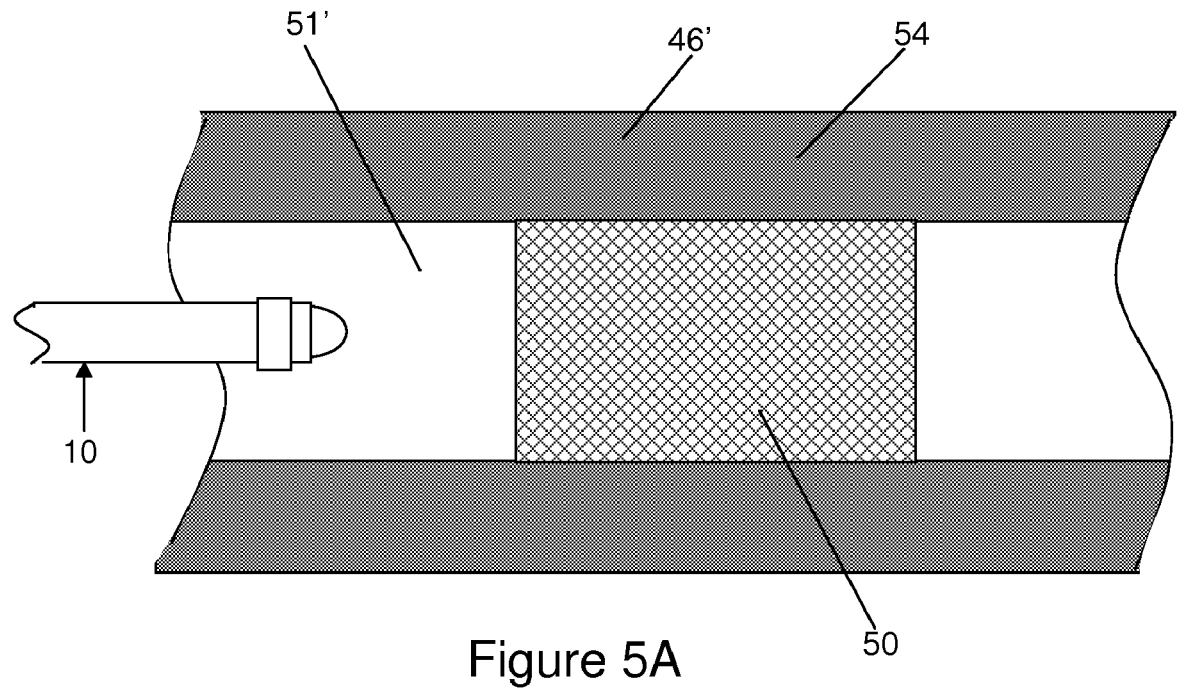
FIGS. 5A through 5E illustrate successive steps in an embodiment of a method of the present invention in which the distal end of the apparatus is steered subintimally to create a channel and then steered back into a lumen of a body vessel.
Figure 5B:
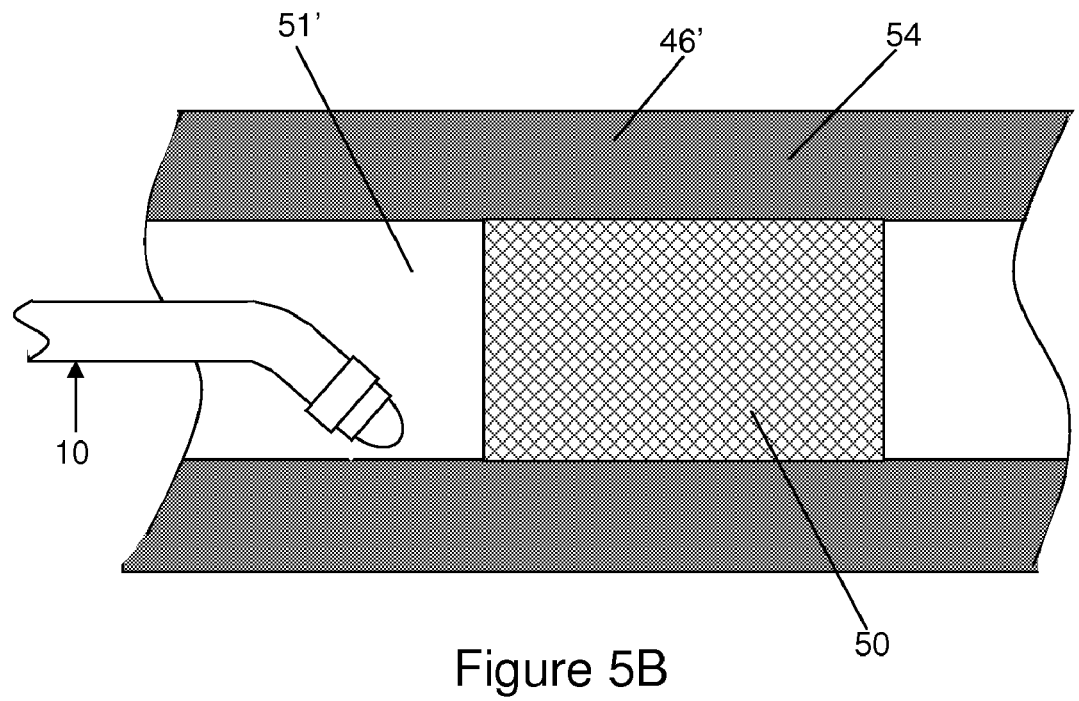
Figure 5C:
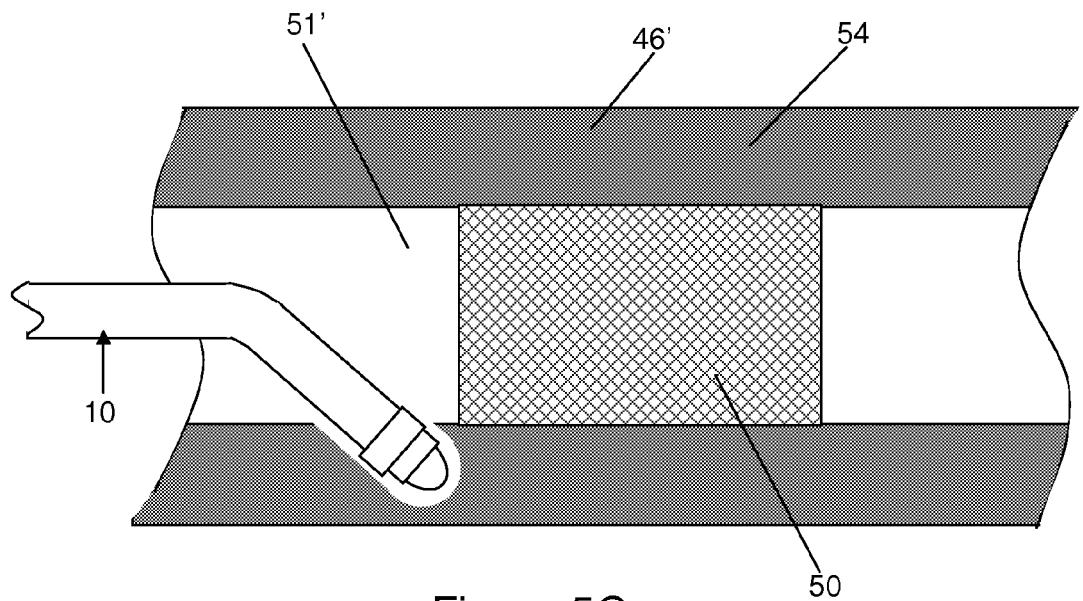
Figure 5D:
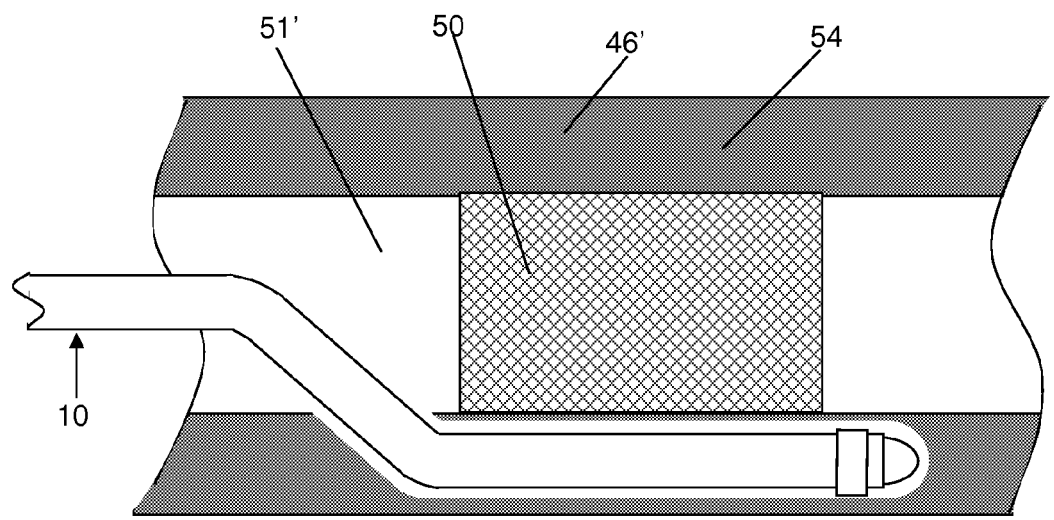
Figure 5E:
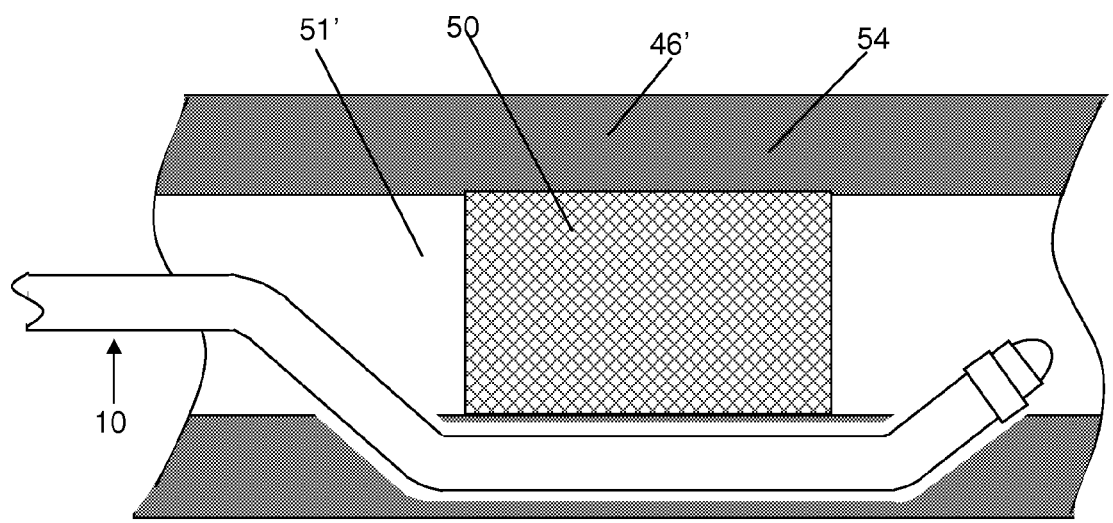
Figure 6A:
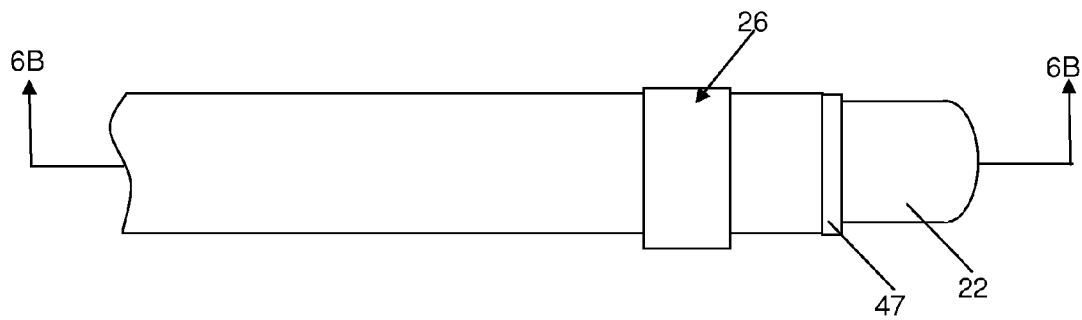
FIG. 6A, in a side elevation view, illustrates an energy delivery apparatus in accordance with another embodiment of the present invention, the energy delivery apparatus including a radiopaque marker.
Figure 6B:
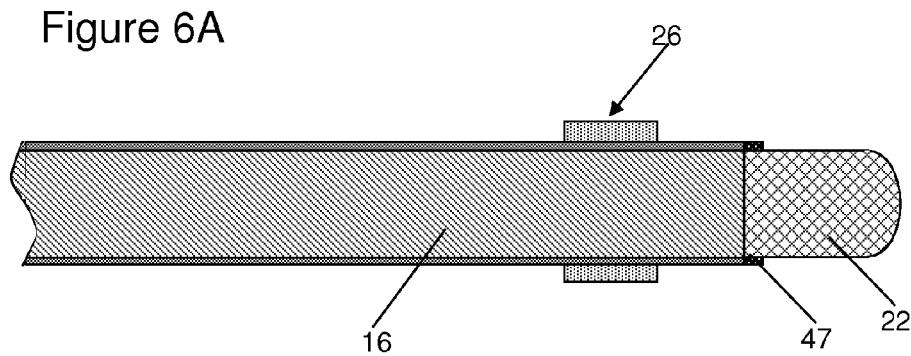
FIG. 6B, in a side cross-sectional view, illustrates the energy delivery apparatus of FIG. 6A.
Figure 6C:
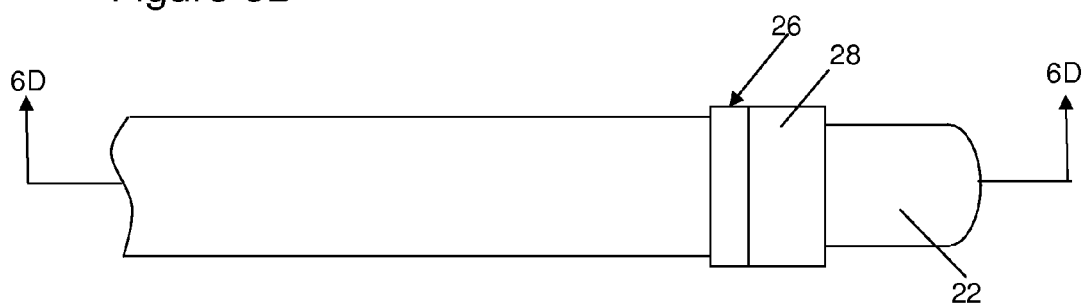
FIG. 6C, in a side elevation view, illustrates an energy delivery apparatus in accordance with yet another embodiment of the present invention, the energy delivery apparatus including a radiopaque marker.
Figure 6D:
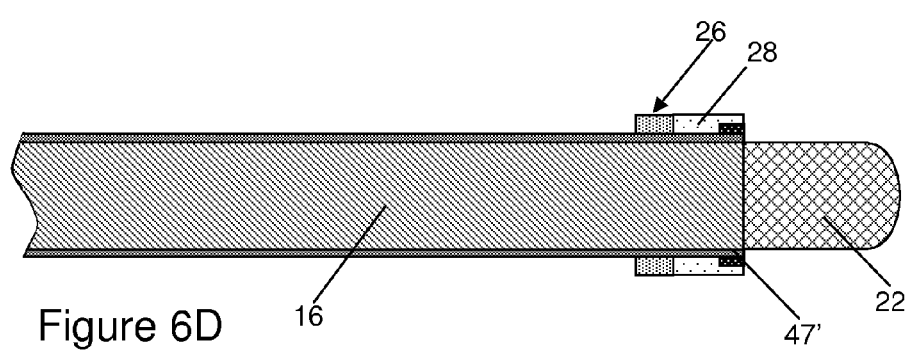
FIG. 6D, in a side cross-sectional view, illustrates the energy delivery apparatus of FIG. 6C.
Figure 6E:
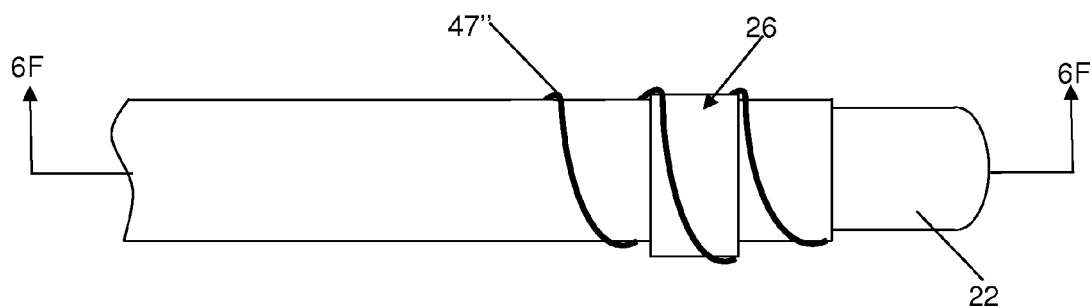
FIG. 6E, in a side elevation view, illustrates an energy delivery apparatus in accordance with yet another embodiment of the present invention, the energy delivery apparatus including a radiopaque marker.
Figure 6F:
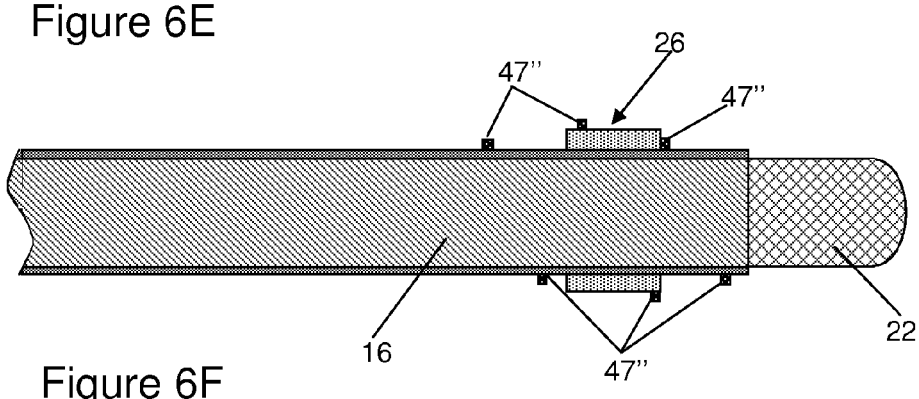
FIG. 6F, in a side cross-sectional view, illustrates the energy delivery apparatus of FIG. 6E.
Figure 7A:
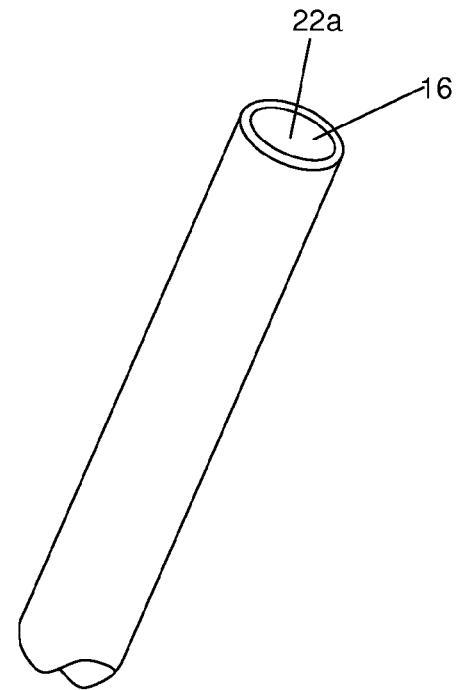
FIGS. 7A to 7D, in partial perspective views, illustrate energy delivery apparatuses in accordance with various embodiments of the present invention, the energy delivery apparatuses differing from each other by a configuration of their electrodes.
Figure 7B:
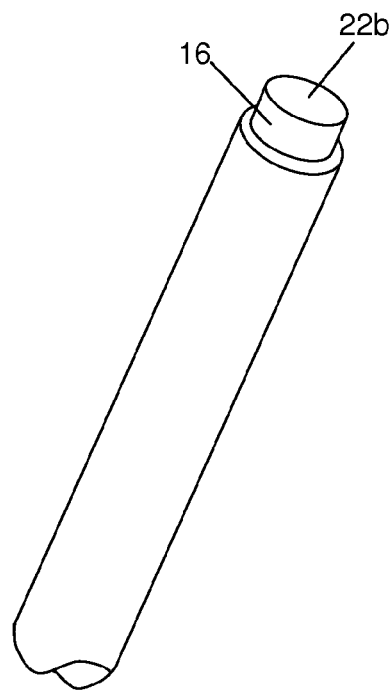
Figure 7C:
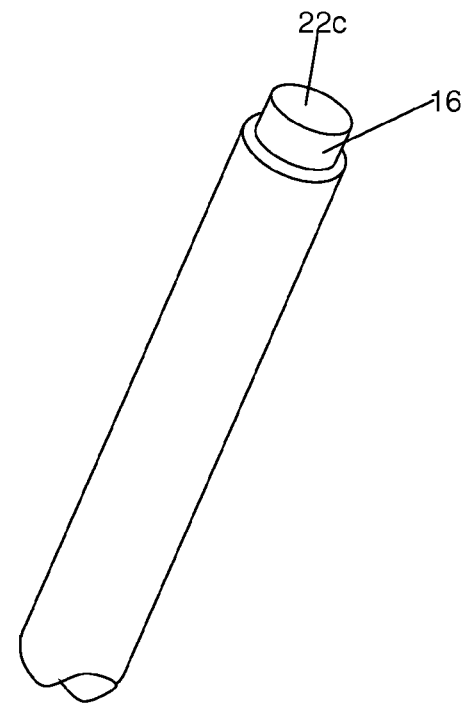
Figure 7D:
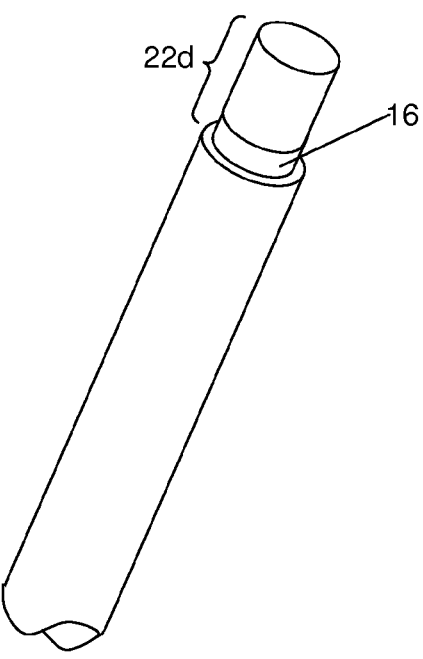

In other examples, as seen in FIGS. 5A to 5E, the application of the magnetic field (as seen in FIG. 5B) allows to relatively easily control the position of the electrode 22 such that the apparatus distal end may be advanced through a section of a vessel wall 54 of the body vessel 46' (as seen in FIGS. 5C and 5D). Afterwards, reversing the orientation of the magnetic field allows to advance the apparatus distal end 14 back into the lumen 51' of the body vessel 46' (as seen in FIG. 5E). This method is particularly advantageous in cases wherein the occlusion present in the body vessel has properties making it relatively difficult to penetrate using the energy delivery apparatus 10. In further embodiments, a channel may be created completely through the vessel wall, such that the energy delivery apparatus exits the vessel wall. For example, this may be useful in applications where it is desired to provide a connection between two vessels.

In some embodiments of the invention, when the intended user of the energy delivery apparatus 10 finds that advancing through the occlusion 50 or any other material becomes relatively difficult, the intended user may retract the apparatus distal end and apply electrical energy while a gap exists between the apparatus distal end and the target location. Then, a channel may be created more easily, for example due to the space created between the electrode 22 and the occlusion 50. Afterwards, the apparatus distal end may then be further advanced through this channel.

It has been found that the claimed energy delivery apparatus is particularly well suited for creating channels in occlusions that are located at a bifurcation in the body vessel. Indeed, in prior art devices, the presence of the occlusion at the bifurcation typically pushes the apparatus distal end 14 of prior art devices through the non-occluded branch of the body vessel, which therefore makes the creation of channels through the occlusion relatively difficult. By using the magnetic field, the apparatus distal end may be oriented such that the electrode 22 remains substantially adjacent to the occlusion until at least a portion of a channel is created into the occlusion which allows the distal end of the energy delivery apparatus to be received within the occlusion, such that the energy delivery apparatus is guided away from the non-occluded branch.

Another use of embodiments of the energy delivery apparatus of the present invention resides in the creation of air pathways in the lungs of the patient. In this case, the body vessel is an airway present in a lung including lung tissue defining airways. By suitably positioning the electrode 22, it is possible to deliver the electrical energy to create an air pathway extending from the airway into the lung tissue.

In specific embodiments of the invention, the electrical conductor 16 is between about 40 centimeters and about 350 centimeters in length. In more specific embodiments of the invention, the electrical conductor 16 is between about 65 centimeters and 265 centimeters in length. The outer diameter of the energy delivery apparatus 10 is typically between about 0.01 inches and about 0.05 inches. In a specific embodiment of the invention, the outer diameter is between about 0.014 inches and about 0.04 inches. In a very specific embodiment of the invention, the electrical conductor 16 has an outer diameter of about 0.0025 inches in the narrower section and 0.012 inches in the wider section. The electrode is typically less than about 4 millimeters in length.

Typical values from the thickness of the electrically insulating materials vary from about 0.015 inches to about 0.05 inches. However, other values are within the scope of the invention. In a specific embodiment of the invention, the thickness of the PTFE is about 0.03 inches.

In some embodiments, the heat shield 28 may be between about 0.05 cm and about 0.20 cm in length, and between 0.025 and about 0.05 cm in thickness. In one particular example, the heat shield material is about 0.1 cm in length, and about 0.035 cm in thickness.

Figure 8A:
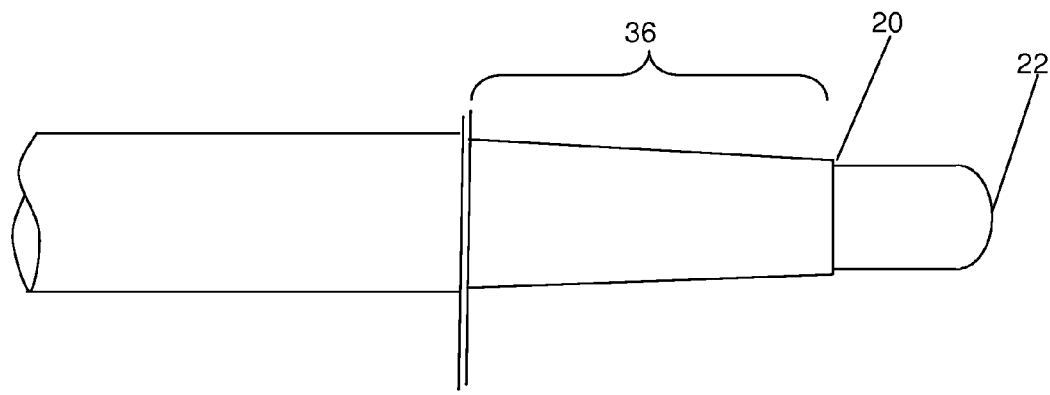
FIGS. 8A to 8C, in partial side elevational views, illustrate energy delivery apparatuses in accordance with various embodiments of the present invention, the energy delivery apparatuses differing from each other by a configuration of their electrical conductors.
Figure 8B:
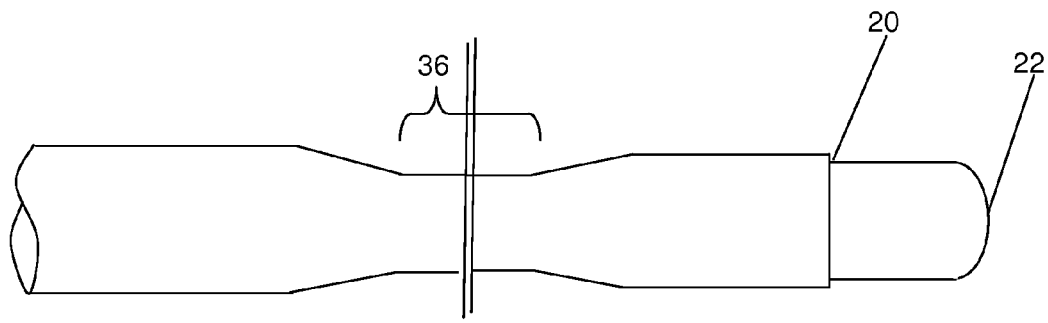
Figure 8C:
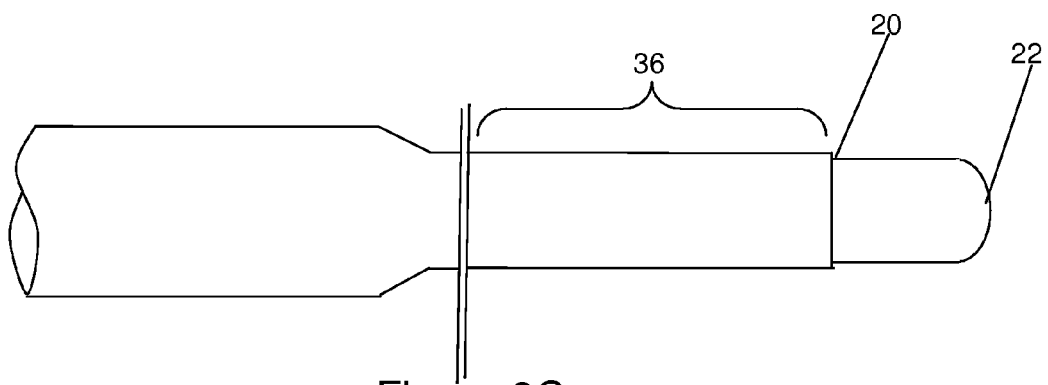

As shown in FIGS. 8A and 8C, the conductor narrower section 36 may be located substantially adjacent the conductor distal end 20. However, in alternative embodiments of the invention, as shown, for example, in FIG. 8B, the conductor narrower section 36 is located substantially spaced apart from the conductor distal end 20. Also, the conductor narrower section 36 may have a substantially uniform diameter or, as shown in FIG. 8A, may have a substantially tapering outer diameter, the outer diameter tapering in a direction, for example, leading towards the conductor distal end 20. These configurations allow to adjust the deformation property of the energy delivery apparatus 10 and, therefore, the deflection of the electrode 22 in response to the application of the magnetic field.

Other manners of affecting the flexibility of the electrical conductor 12 and, more specifically, of the energy delivery apparatus 10 include the formation of notches in the electrically insulating material, in the electrical conductor 16 or both in the electrical conductor 16 and the electrically insulating material.

In some embodiments of the invention, the magnetically responsive material is welded, soldered, adhered or otherwise attached to the conductor distal end 20.

Figure 9:
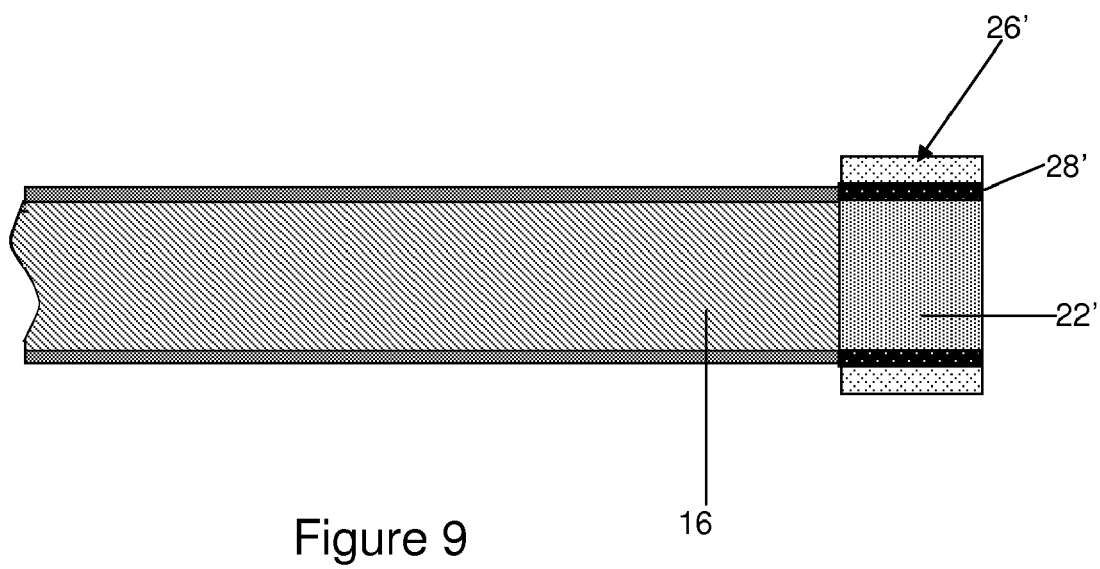
FIG. 9, in a side cross-sectional view, illustrates an energy delivery apparatus in accordance with yet another embodiment of the present invention.

In yet other embodiments of the invention, as shown in FIG. 9, the guiding element 26' is substantially radially spaced apart from the electrode 22', the heat shield 28' extending therebetween.

As seen respectively in FIGS. 7A, 7B, 7C and 7D, the electrode 22a, 22b, 22c and 22d may take the form of a distal surface of the electrical conductor 16 that is deprived of insulating material, a cylindrical section of the electrical conductor 16 that is deprived of insulating material, an electrically conductive component, for example a stainless steel cylinder, which is electrically coupled to conductor 16, or a combination of a conductive component and a section of the conductor 16.

In some embodiments, an auxiliary device may be advanced to the target location by using the energy delivery apparatus 10 as a guide or a rail. In some such embodiments, the apparatus proximal end may be passed through the auxiliary device, and the auxiliary device may then be advanced together with energy delivery apparatus 10 into the patient's body. In alternate embodiments, the auxiliary device may be inserted over energy delivery apparatus 10 and into the patient's body after energy delivery apparatus 10 has reached the target location. Examples of auxiliary devices include, but are not limited to, catheters, sheaths, dilators, visualization devices, or any other devices having a lumen within which energy delivery apparatus 10 may be disposed.

In some embodiments, the energy delivery apparatus 10 may comprise means for enhancing steerability. Such means may include piezo-actuators or electroactive polymers disposed on the distal region of the energy delivery apparatus 10. For example, a piezo-actuator or electroactive polymer may be disposed on one side of the energy delivery apparatus 10, such that when an electrical field is applied across the piezo-actuator or electroactive polymer, a strain is generated along one side of the energy delivery apparatus 10, causing the energy delivery apparatus 10 to deflect in a desired direction.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the present invention has been described hereinabove by way of certain embodiments thereof, it can be modified, without departing from the subject invention as defined in the appended claims.

We claim:

1. An energy delivery apparatus for delivering electrical energy at a target location, said energy delivery apparatus being usable in combination with a magnetic field, said energy delivery apparatus comprising:
   an electrical conductor, said electrical conductor having an elongated configuration;
   an electrode for delivering said electrical energy at said target location, said electrode being electrically coupled to said electrical conductor and located at a predetermined location therealong; and
   a guiding element mounted to said electrical conductor in a longitudinally spaced apart relationship relative to said electrode, said guiding element including at least two guiding components longitudinally spaced apart relative to each other, each of said guiding components being mounted to said electrical conductor and including a respective magnetically responsive material;
   wherein said energy delivery apparatus is constructed such that movement of said guiding element causes a corresponding movement of said electrode;
   whereby said magnetic field is used to move said guiding element in order to position said electrode adjacent to said target location.

2. An energy delivery apparatus as defined in claim 1, further comprising a heat shield made out of a thermally insulating material, said heat shield being located, at least in part, between said electrode and said guiding element.

3. An energy delivery apparatus as defined in claim 2, wherein said thermally insulating material is polytetrafluoroethylene (PTFE).

4. An energy delivery apparatus as defined in claim 2, wherein said heat shield extends longitudinally from said electrode.

5. An energy delivery apparatus as defined in claim 1, wherein said electrical conductor defines a conductor proximal end and a longitudinally opposed conductor distal end, said electrical conductor being more flexible adjacent said conductor distal end than adjacent said conductor proximal end.

6. An energy delivery apparatus as defined in claim 1, further comprising an electrically insulating material covering said electrical conductor, said electrode being deprived of said electrically insulating material.

7. An energy delivery apparatus as defined in claim 6, further comprising
   a first electrically insulating layer made out of a first electrically insulating material, said first electrically insulating layer covering a first section of said electrical conductor; and
   a second electrically insulating layer made out of a second electrically insulating material, said second electrically insulating layer covering a second section of said electrical conductor, said second section being located distally relatively to said first section;
   wherein said second electrically insulating layer is thinner than said first electrically insulating layer.

8. An energy delivery apparatus as defined in claim 6, wherein said first electrically insulating material is more lubricious than said second electrically insulating material.

9. An energy delivery apparatus as defined in claim 1, wherein said electrode is located adjacent to said conductor distal end.

10. A method for delivering electrical energy at a target location using an energy delivery apparatus, said method using a magnetic field, said target location being located in a body of a patient, said body including a body vessel, said energy delivery apparatus being elongated, said energy delivery apparatus defining an apparatus proximal end and a longitudinally opposed apparatus distal end, said energy delivery apparatus including an elongated electrical conductor, an electrode electrically coupled to said electrical conductor and a magnetically responsive material mounted to said electrical conductor; said method comprising:
    inserting said apparatus distal end into said body vessel;
    applying said magnetic field to exert a magnetic force onto said magnetically responsive material so as to move said electrode;
    guiding said electrode to an electrode location, said electrode location being adjacent to said target location; and
    delivering said electrical energy at said target location through said electrode;
    wherein said body vessel defines a vessel wall, said method further comprising advancing said apparatus distal end through a section of said vessel wall.

11. A method as defined in claim 10, further comprising advancing said apparatus distal end back into said body vessel after advancing said apparatus distal end through said section of said vessel wall.

12. An energy delivery apparatus for delivering electrical energy at a target location, said energy delivery apparatus being usable in combination with a magnetic field, said energy delivery apparatus comprising:
    an electrical conductor, said electrical conductor having an elongated configuration;

said electrical conductor defining a conductor wider section and a conductor narrower section, said conductor narrower section being positioned distally relatively to said conductor wider section, said conductor wider section having a cross-sectional area larger than a cross-sectional area of said conductor narrower section;

an electrode for delivering said electrical energy at said target location, said electrode being electrically coupled to said electrical conductor and located at a predetermined location therealong; and a guiding element mounted to said conductor narrower section in a longitudinally spaced apart relationship relative to said electrode, said guiding element including a magnetically responsive material;

wherein said energy delivery apparatus is constructed such that movement of said guiding element causes a corresponding movement of said electrode; whereby said magnetic field is used to move said guiding element in order to position said electrode adjacent to said target location.

13. An energy delivery apparatus as defined in claim 12, wherein a distal region of said energy delivery apparatus has a constant outer diameter, said distal region including said conductor narrower section and at least a portion of said conductor wider section.

14. An energy delivery apparatus as defined in claim 12, further comprising a heat shield made out of a thermally insulating material, said heat shield being located, at least in part, between said electrode and said guiding element.

15. An energy delivery apparatus as defined in claim 12, wherein said electrical conductor defines a conductor proximal end and a longitudinally opposed conductor distal end, said electrical conductor being more flexible adjacent said conductor distal end than adjacent said conductor proximal end.

* * * * *